United States Patent
Gellman (10) Patent No.: US 10,201,441 B2
(45) Date of Patent: Feb. 12, 2019

(54) LINEARLY EXPANDABLE URETERAL STENT

(75) Inventor: Barry N. Gellman, N. Easton, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 978 days.

(21) Appl. No.: 12/628,289

(22) Filed: Dec. 1, 2009

(65) Prior Publication Data

US 2010/0076574 A1 Mar. 25, 2010

Related U.S. Application Data

(62) Division of application No. 12/241,450, filed on Sep. 30, 2008, now Pat. No. 9,060,888, which is a division of application No. 10/283,873, filed on Oct. 30, 2002.

(51) Int. Cl.
  *A61F 2/04* (2013.01)
  *A61F 2/88* (2006.01)
  *A61M 27/00* (2006.01)

(52) U.S. Cl.
  CPC .............. *A61F 2/88* (2013.01); *A61F 2/04* (2013.01); *A61M 27/008* (2013.01)

(58) Field of Classification Search
  CPC .......... A61F 2/04; A61F 2/022; A61F 2/0063; A61F 2/02; A61F 2/07; A61F 2/88; A61F 2230/0091; A61M 27/008
  USPC ............................. 623/23.64–23.71, 8, 11.11
  See application file for complete search history.

(56) References Cited

U.S. PATENT DOCUMENTS

| | | | |
|---|---|---|---|
| 550,238 | A | 11/1895 | Allen, Jr. |
| 3,695,021 | A | 10/1972 | Ormerod et al. |
| 4,503,569 | A | 3/1985 | Dotter |
| 4,531,933 | A | 7/1985 | Norton et al. |
| 4,643,716 | A | 2/1987 | Drach |
| 4,660,560 | A | 4/1987 | Klein |
| 4,671,795 | A | 6/1987 | Mulchin |
| 4,681,570 | A | 7/1987 | Dalton |

(Continued)

FOREIGN PATENT DOCUMENTS

| | | |
|---|---|---|
| DE | 101 55 767 A1 | 5/2003 |
| WO | 2001089415 A2 | 11/2001 |
| WO | 2005102217 A1 | 11/2005 |

OTHER PUBLICATIONS

Non-Final Office Action for U.S. Appl. No. 12/241,450, dated Sep. 16, 2010, 13 pages.

(Continued)

*Primary Examiner* — Paul Prebilic (57) ABSTRACT

A ureteral stent includes an elongated member, which has a tubular shape, and a distal retention structure. The elongated member includes a sidewall that defines a lumen and has a spiral-shaped opening with at least two rotations. The sidewall has an inner surface and an outer surface. The sidewall between the inner surface and the outer surface is devoid of another lumen. The elongated member is configured to move between a retracted configuration and an expanded configuration along a longitudinal axis of the lumen. The distal retention structure is disposed at a distal end of the elongated member for retention in a kidney. The distal retention structure defines a lumen in fluid communication with the lumen defined by the sidewall of the elongated member.

14 Claims, 7 Drawing Sheets

(56) References Cited

U.S. PATENT DOCUMENTS

| | | | |
|---|---|---|---|
| 4,813,925 A | 3/1989 | Anderson, Jr. et al. | |
| 4,874,360 A | 10/1989 | Goldberg et al. | |
| 5,057,114 A | 10/1991 | Wittich et al. | |
| 5,059,169 A | 10/1991 | Zilber | |
| 5,098,440 A | 3/1992 | Hillstead | |
| 5,116,309 A | 5/1992 | Coll | |
| 5,129,910 A * | 7/1992 | Phan et al. | 606/127 |
| 5,282,860 A | 2/1994 | Matsuno et al. | |
| 5,514,176 A | 5/1996 | Bosley, Jr. | |
| 5,531,741 A | 7/1996 | Barbacci | |
| 5,554,189 A | 9/1996 | De La Torre | |
| 5,562,641 A | 10/1996 | Flomenblit et al. | |
| 5,562,678 A | 10/1996 | Booker | |
| 5,572,819 A | 11/1996 | Topinka et al. | |
| 5,599,291 A | 2/1997 | Balbierz et al. | |
| 5,613,973 A | 3/1997 | Jackson et al. | |
| 5,647,843 A | 7/1997 | Mesrobian et al. | |
| 5,681,274 A | 10/1997 | Perkins et al. | |
| 5,782,916 A | 7/1998 | Pintauro et al. | |
| 5,789,047 A | 8/1998 | Sasaki et al. | |
| 5,795,319 A | 8/1998 | Ali | |
| 5,814,006 A | 9/1998 | Planz | |
| 5,827,321 A | 10/1998 | Roubin et al. | |
| 5,944,701 A | 8/1999 | Dubrul | |
| 5,962,007 A | 10/1999 | Cooper et al. | |
| 5,964,744 A | 10/1999 | Balbierz et al. | |
| 6,019,779 A | 2/2000 | Thorud et al. | |
| 6,027,516 A | 2/2000 | Kolobow et al. | |
| 6,059,825 A * | 5/2000 | Hobbs et al. | 623/1.18 |
| 6,171,338 B1 * | 1/2001 | Talja et al. | 623/1.22 |
| 6,214,042 B1 | 4/2001 | Jacobsen et al. | |
| 6,241,691 B1 | 6/2001 | Ferrera et al. | |
| 6,258,119 B1 * | 7/2001 | Hussein et al. | 623/1.22 |
| 6,306,105 B1 | 10/2001 | Rooney et al. | |
| 6,332,892 B1 | 12/2001 | Desmond, III et al. | |
| 6,395,021 B1 | 5/2002 | Hart et al. | |
| 6,458,145 B1 | 10/2002 | Ravenscroft et al. | |
| 6,620,202 B2 | 4/2003 | Bottcher et al. | |
| 6,558,349 B1 | 5/2003 | Kirkman | |
| 6,569,150 B2 | 5/2003 | Teague et al. | |
| 6,648,912 B2 | 11/2003 | Trout, III et al. | |
| 6,685,744 B2 | 2/2004 | Gellman et al. | |
| 6,719,804 B2 | 4/2004 | St Pierre | |
| 6,733,536 B1 | 5/2004 | Gellman | |
| 6,887,215 B2 | 5/2005 | McWeeney | |
| 6,913,625 B2 | 7/2005 | Segura et al. | |
| 6,929,664 B2 | 8/2005 | Kolb | |
| 6,976,973 B1 | 12/2005 | Ruddell et al. | |
| 7,041,139 B2 | 5/2006 | Bluni et al. | |
| 7,044,981 B2 | 5/2006 | Liu et al. | |
| 7,166,134 B2 | 1/2007 | Datta et al. | |
| 7,169,187 B2 | 1/2007 | Datta et al. | |
| 7,320,674 B2 | 1/2008 | Ruddell et al. | |
| 7,507,218 B2 | 3/2009 | Aliski et al. | |
| 7,550,012 B2 | 6/2009 | Lavelle | |
| 8,007,702 B2 | 8/2011 | Gellman | |
| 8,241,548 B2 | 8/2012 | Gellman | |
| 8,568,643 B2 | 10/2013 | Gellman | |
| 9,017,395 B2 * | 4/2015 | Peckham | A61F 2/88 623/1.22 |
| 2001/0003801 A1 | 6/2001 | Strecker | |
| 2001/0053936 A1 | 12/2001 | Whitmore | |
| 2002/0177899 A1 | 11/2002 | Eum et al. | |
| 2002/0183852 A1 | 12/2002 | McWeeney | |
| 2003/0040803 A1 | 2/2003 | Rioux et al. | |
| 2003/0060870 A1 * | 3/2003 | Reever | 623/1.12 |
| 2003/0163204 A1 | 8/2003 | Rix | |
| 2003/0171708 A1 | 9/2003 | Segura et al. | |
| 2003/0176831 A1 | 9/2003 | Gellman et al. | |
| 2003/0181842 A1 | 9/2003 | Gellman | |
| 2003/0191492 A1 | 10/2003 | Gellman et al. | |
| 2003/0195456 A1 | 10/2003 | Robertson | |
| 2003/0199805 A1 | 10/2003 | McWeeney | |
| 2005/0131547 A1 | 6/2005 | Segura et al. | |
| 2009/0030363 A1 | 1/2009 | Gellman | |
| 2010/0072659 A1 | 3/2010 | Gellman | |
| 2012/0285607 A1 | 11/2012 | Gellman | |
| 2018/0125684 A1 * | 5/2018 | DeGraaf | A61F 2/042 |

OTHER PUBLICATIONS

Non-Final Office Action Response for U.S. Appl. No. 12/241,450, filed Jan. 21, 2011, 12 pages.

Non-Final Office Action for U.S. Appl. No. 12/628,304, dated Dec. 10, 2010, 13 pages.

Non-Final Office Action for U.S. Appl. No. 12/241,450, dated Jun. 22, 2010, 6 pages.

Office Action Response for U.S. Appl. No. 12/241,450, filed Jul. 22, 2010, 2 pages.

Final Office Action Response for U.S. Appl. No. 12/241,450, filed May 9, 2011, 12 pages.

Advisory Action for U.S. Appl. No. 12/241,450, dated May 19, 2011, 3 pages.

Final Office Action for U.S. Appl. No. 12/241,450, dated Mar. 10, 2011, 14 pages.

Notice of Allowance for U.S. Appl. No. 12/628,304, dated Apr. 28, 2011, 15 pages.

U.S. Appl. No. 60/136,177, filed May 27, 1999, Tremaglio.

Thomas W. Duerig et al. "Superelastic Nitinol for Medical Devices," Medical Device Link. [online] [retrieved on Aug. 7, 2008] Retrieved from the Internet <URL: http://www.devicelink.com/mpb/archive/97/03/003.html>.

Mardis et al., "Ureteral Stents," *Urologic Clinics of North America*, vol. 15, No. 3, Aug. 1988, pp. 471-479.

Kulkarni et al., "An analysis of the cost effectiveness of a new thermo expandable ureteric stent MEMOKATH® 051," presented at the 1999 World Congress on Endourology at the Ashford Hospital, Ashford, Middlesex, United Kingdom, 1 page.

Kulkarni etal., "A critical evaluation of the indications and long term results of the application of MEMOKATH® 051," presented at the 2000 World Congress on Endourology at the Ashford and St. Peter's Hospital, Ashford, Middlesex, United Kingdom, 1 page.

International Search Report for International Application No. PCT/US03/34214 dated Apr. 15, 2004.

Barwart et al., "An evaluation of the transition temperature range of super-elastic orthodontic NiTi springs using differential scanning calorimetry," European Journal of Orthodontics 21:497-502 (1999).

Notice of Allowance for U.S. Appl. No. 13/205,440, dated Apr. 13, 2012, 23 pages.

Non-Final Office Action for U.S. Appl. No. 12/241,450, dated Oct. 31, 2013, 13 pages.

Notice of Allowance for U.S. Appl. No. 13/556,864, dated Jun. 28, 2013, 8 pages.

Final Office Action for U.S. Appl. No. 12/241,450, dated Mar. 4, 2014, 10 pages.

* cited by examiner

LINEARLY EXPANDABLE URETERAL STENT

CROSS-REFERENCE TO RELATED APPLICATIONS

This application is a divisional of U.S. patent application Ser. No. 12/241,450, entitled "Linearly Expandable Ureteral Stent," filed September 30, 2008, now U.S. Pat. No. 9,060,888, which is a divisional of U.S. patent application Ser. No. 10/283,873, entitled "Linearly Expandable Ureteral Stent," filed October 30, 2002, now abandoned, both of which are incorporated herein by reference in their entirety.

BACKGROUND

The invention generally relates generally to medical devices for the drainage of fluids, and more specifically to ureteral stents.

A ureter is a tubular passageway in a human body that conveys urine from a kidney to a bladder. The ureter begins with the renal pelvis and ends at the trigone region of the bladder, i.e., the triangulated area between both ureteral orifices and the bladder neck. Urine is transported through the ureter under the influence of hydrostatic pressure, assisted by contractions of muscles located within the walls (lining) of the ureter. Some patients experience a urological condition known as ureteral blockage or obstruction. Some common causes of ureteral blockage are the formation of tumors or abnormalities within the ureteral lining, or the formation and passage of kidney stones.

Ureteral stents are used to facilitate urinary drainage from the kidneys to the bladder in patients having a ureteral obstruction or injury, or to protect the integrity of the ureter in a variety of surgical manipulations. Stents may be used to treat or avoid ureter obstructions (such as ureteral stones or ureteral tumors) which disrupt the flow of urine from the kidneys to the bladder. Serious obstructions may cause urine to back up into the kidneys, threatening renal function. Ureteral stents may also be used after endoscopic inspection of the ureter.

A stent may be uncomfortable to a patient because of intramural tunnel pain, imposed by the stent itself or in combination with intraoperative trauma inflicted from device passage. Pain may also be caused by urine reflux back up the ureter during increased bladder pressure, e.g., during voiding. Further, pain may stem from trigome irritation resulting from constant irritation, imposed by the bladder anchoring features or in combination with intraoperative trauma inflicted from device passage. Moreover, discomfort may arise from flank pain, caused by reflux or kidney anchoring.

Ureteral stents typically are tubular in shape, terminating in two opposing ends: a kidney distal end and a bladder proximal end. Existing ureteral stents compensate for the motion between the kidney and bladder by employing a pair of coil end-effectors, with one effector placed in the bladder proximal end and the other in the kidney distal end. As motion occurs, the ureter slides up and down the stent body. Any other travel results in an uncurling of the end effector(s).

SUMMARY

It is an objective of the invention to provide a patient, male or female, with a flexible device designed to maintain the patency of the ureter and enable fluid drainage while minimizing the pains and discomfort commonly associate with an in-dwelling device.

Discomfort may be related to the stent rubbing against a wall of the ureter, caused by the constant relative motion between the kidney and the bladder. This motion may be as much as 5 centimeters (cm) (approximately 2 inches) and cycles with each breath of the patient. This is equal to approximately 17,000 cycles per day, assuming 1 breath every 5 seconds. The present invention alleviates discomfort by providing a stent that, like the ureter, linearly expands and contracts in response to relative motion between the kidney and the bladder, thereby reducing friction caused by a stent rubbing against a wall of the ureter.

In one aspect, the invention features a ureteral stent having an elongated member defining a lumen. The member has a solid sidewall defining a spiral-shaped opening such that the member is linearly expandable along a longitudinal axis of the lumen. A distal retention structure is connected to a distal end of the elongated member for retention in a kidney, and a proximal retention structure is connected to a proximal end of the elongated member for retention in a bladder.

One or more of the following features may also be included. The member includes a spring having a spring force of less than one pound. The member includes a wire spring. The wire spring includes a metal alloy, that may include at least one of titanium, nickel, copper, cobalt, vanadium, and iron. The metal alloy includes nitinol. The wire spring is coated with a polymer. The polymer includes at least one of urethane, nylon, thermoplastic polyurethane (TPU), thermoplastic polyester elastomer, polyethyl, and silicone.

The stent has an elongated member including a tube having the solid sidewall and defining the lumen. The spiral-shaped opening is defined by a slit formed in the sidewall of the tube. The elongated member may include a polymer, such as at least one of urethane, nylon, TPU, thermoplastic polyester elastomer, polyethyl, and silicone.

The elongated member includes an inner liner and an outer cover. A wire spring is sandwiched between the inner liner and the outer cover, with the spiral-shaped opening being defined by slits formed in the inner liner and the outer cover, between a plurality of coils of the wire spring. The wire spring includes a metal alloy including, e.g., at least one of titanium, nickel, copper, cobalt, vanadium, and iron. The metal alloy includes nitinol. At least one of the inner liner and the outer cover includes a polymer. The polymer includes at least one of urethane, nylon, TPU, thermoplastic polyester elastomer, polyethyl, and silicone.

A removable introducer is sized for placement within the lumen.

In another aspect of the invention, a ureteral stent includes an elongated member defining a lumen, the member having a solid sidewall with at least one slit formed therein such that the member is linearly expandable along a longitudinal axis of the lumen. A distal retention structure is connected to a distal end of the elongated member for retention in a kidney, and a proximal retention structure is connected to a proximal end of the elongated member for retention in a bladder.

In yet another aspect of the invention, a method of facilitating urinary drainage from a kidney to a bladder in a patient that reduces discomfort to the patient includes positioning a ureteral stent in a ureter of a patient, the ureteral stent having an elongated member defining a lumen, the member having a solid sidewall defining a spiral-shaped opening such that the member is linearly expandable along a longitudinal axis of the lumen, a distal retention structure connected to a distal end of the elongated member for retention in the kidney, and a proximal retention structure connected to a proximal end of the elongated member for retention in the bladder. The elongated member is allowed to linearly expand and contract between an expanded position and a retracted position, based on at least one of: relative positioning of organs within the patient, a breathing pattern of the patient, and relative positions of the kidney and the bladder. In addition, the elongated member can be biased to the retracted position.

In yet another aspect of the invention, a method of manufacturing a linearly expandable ureteral stent includes providing an elongated member defining a lumen, the member having a solid sidewall defining a spiral-shaped opening such that the member is linearly expandable along a longitudinal axis of the lumen. The stent also includes a distal retention structure and a proximal retention structure. The distal retention structure is connected to a distal end of the elongated member, and the proximal retention structure is connected to a proximal end of the elongated member.

The following features may be included. Providing the elongated member includes providing a wire spring. Providing the wire spring includes coating the wire spring with a polymer. Providing the wire spring includes sandwiching the wire spring between an inner lining and an outer cover. The inner lining and outer cover include extruded sheets. The inner lining and outer cover are shrunk, and slits are formed through the inner lining and outer cover between a plurality of coils of the wire spring. The inner lining and the outer cover are melted, and slits are formed through the inner lining and outer cover between a plurality of coils of the wire spring. The elongated member is provided by forming a tube including a polymer, and forming a spiral slit through the tube.

In yet another aspect of the invention, a method of placing a ureteral stent in a patient includes providing a ureteral stent. The ureteral stent includes an elongated member defining a lumen, the member having a solid sidewall defining a spiral-shaped opening such that the member is linearly expandable along a longitudinal axis of the lumen. The ureteral stent also includes a distal retention structure connected to a distal end of the elongated member, and a proximal retention structure connected to a proximal end of the elongated member. The ureteral stent is inserted into a ureter of the patient. The ureteral stent is positioned in the patient with the distal retention structure substantially within the kidney of the patient, the elongated member substantially within the intramural tunnel portion of the ureter, and the proximal retention structure substantially within the bladder of the patient. In a detailed embodiment, the ureteral stent can further include a removable introducer sized to fit within the lumen and inserting the ureteral stent includes inserting the stent with the removable introducer into the ureter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

The invention features temporary ureteral stents that, when positioned within the ureter of a patient, significantly reduce discomfort to the patient. As used herein, proximal refers to the end of a stent closest to a medical professional when placing a stent in a patient. As used herein, distal refers to the end of a stent furthest from a medical professional when placing a stent in a patient.

Figures 1A, 1B, 1C:
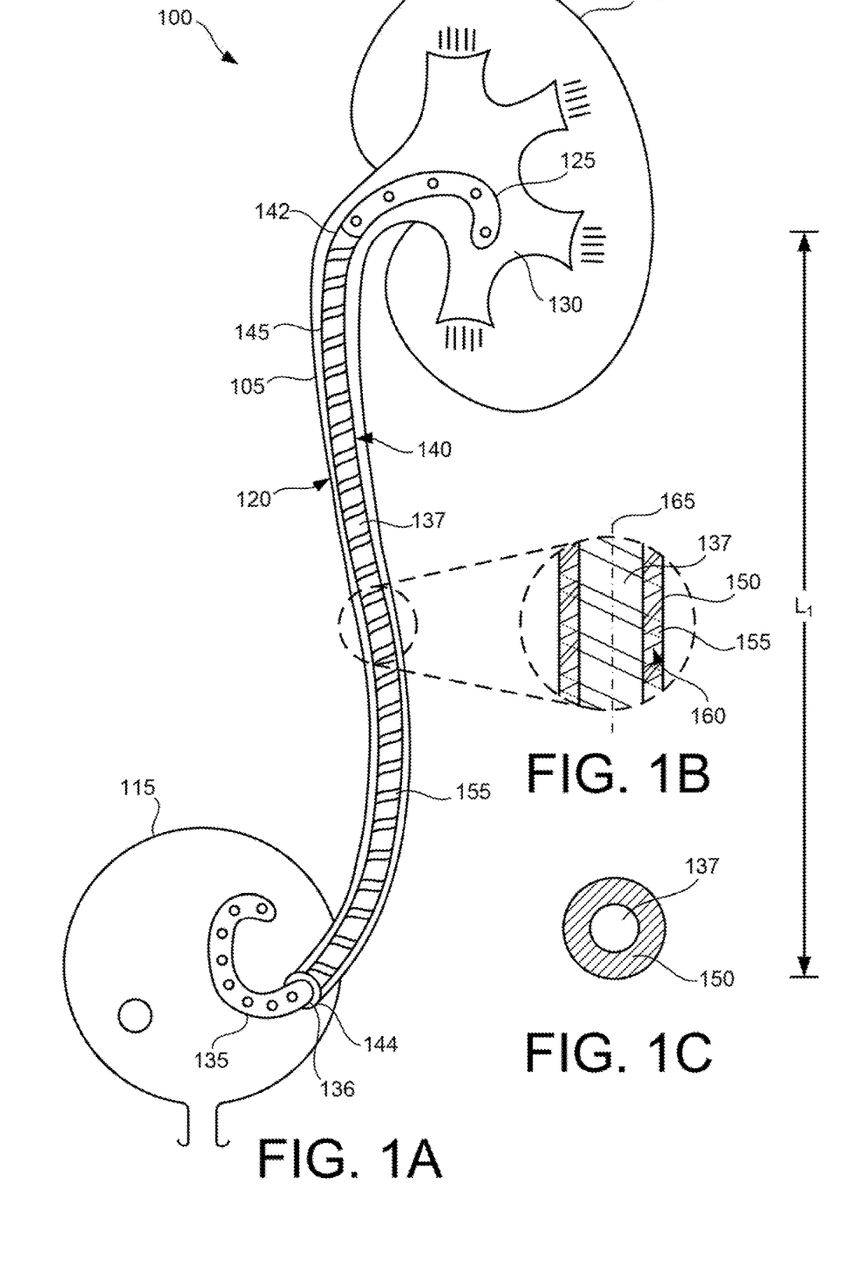
FIG. 1A is a schematic view of a human urinary tract, illustrating the placement of one embodiment of the invention within the ureter of a patient, in an expanded position.
FIGS. 1B-1C are detailed views of a portion of the embodiment of the invention of FIG. 1A.

Referring to FIG. 1A, a human urinary tract 100 includes a ureter 105 that transports urine from a kidney 110 to a bladder 115. When ureter 105 becomes blocked or obstructed due to, for example, post-kidney stone fragmentation/removal and ureteral stricture therapy, fluid drainage can become restricted. Ureteral stents are medical devices that are implanted within ureter 105 to restore patency and fluid drainage. A ureteral stent 120 is located within the ureter 105 of a patient, with a distal retention structure 125 in a pelvis 130 of kidney 110, and a proximal retention structure 135 in the bladder 115, proximate ureteral orifice 136. A lumen 137 extends within distal retention structure 125, an elongated member 140, and proximal retention structure 135 to provide for the passage of fluid. Distal retention structure 125 is connected to a distal end 142 of elongated member 120, and proximal retention structure 135 is connected to a proximal end 144 of elongated member 140. Distal retention structure 125 secures distal end 142 of elongated member in or proximate to kidney 110. Proximal retention structure 135 secures proximal end 144 of elongated member 140 in or proximate bladder 115, as well as facilitates the removal of stent 120 by providing a loop suitable for grasping by a hook.

Distal retention structure 125 and proximal retention structure 135 can be fabricated of materials such as nylon, polyurethane, or the like. Heat bonding of these materials to elongated member 140 is conveniently accomplished by, for example, using an RF heat source as is commonly employed for plastic tubes and catheters. The desired shape of distal and proximal retention structures 125, 135 can be formed by injection molding or extrusion. They can also be heat-formed, for example, by flaring the working piece over an anvil of an appropriate shape, with the application of heat. The shape of distal retention structure 125 can be, for example, a coil, a pig-tail coil, J-shaped, or a helical coil. The shape of proximal retention structure 135 can be, for example, a coil, a pig-tail coil, J-shaped or a helical coil. In the illustrated embodiment, both distal and proximal retention structures 125, 135 are J-shaped.

Referring to FIGS. 1A-1C, elongated member 140 includes a tube 145 having a solid sidewall 150. A slit 155 is formed in sidewall 150, defining a spiral-shaped opening 160, so that elongated member 140 is linearly expandable along a longitudinal axis 165 of lumen 137. Elongated member 140 can be formed from a polymer, such as, e.g., urethane, nylon, TPU, thermoplastic polyester elastomer, polyethyl, and silicone.

Elongated member 140 can be manufactured by, for example, injection molding or extrusion and optionally a combination of subsequent machining operations. Extrusion processes, for example, can be used to provide a uniform shape, such as a single monolithic tube. Spiral-shaped opening 160 can be created in the desired locations by a subsequent machining operation.

Figures 2A, 2B:
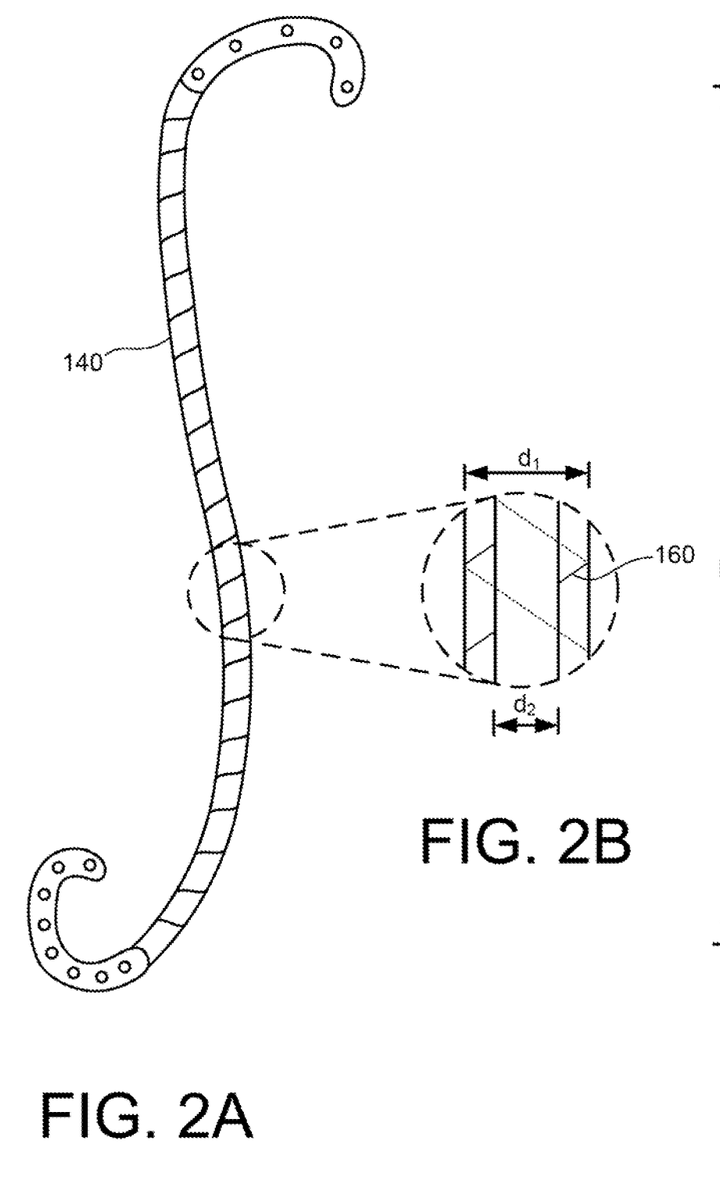
FIGS. 2A-2B are schematic representations of the embodiment of the invention illustrated in FIGS. 1A-1C in a retracted position.

Referring also to FIGS. 2A and 2B, elongated member 140 is linearly expandable between an expanded position (see, e.g., FIGS. 1A-1B) and a retracted position (see FIGS. 2A-2B). When elongated member 140 is retracted, spiral-shaped opening 160 is closed. A difference in an expanded length $L_1$ of elongated member 140 in its expanded position and a retracted length $L_2$ of elongated member 140 in its retracted position can be approximately 5 cm (approximately 2 inches). For example, elongated member 140 can be sized so that retracted length $L_2$ is approximately 8 cm to 30 cm, and expanded length $L_1$ is approximately 13 cm to 35 cm. Elongated member 140 can have, in its retracted position, an outer diameter $d_1$ corresponding to approximately 3.7 French to 14.0 French. Lumen 137 can have a diameter $d_2$ when elongated member 140 is in its retracted position, to allow the introduction of a guide wire.

In use, elongated member 140 can expand linearly up to 2 inches to expanded length $L_1$, to provide comfort to the patient by compensating for at least one of: relative positioning of organs within the patient, a breathing pattern of the patient, and relative positions of kidney 110 and bladder 115. Because of the possibility of linear expansion, a physician may be able to select ureteral stent 120 with a smaller size than would be required with a conventional stent.

Figures 3A, 3B:
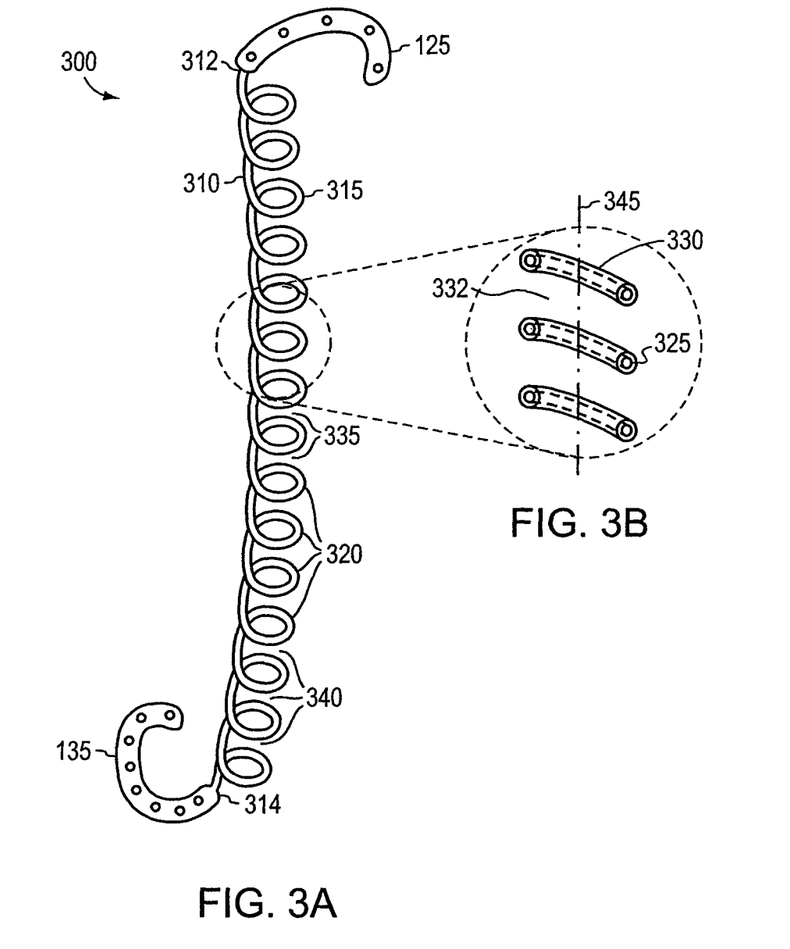
FIGS. 3A-3B are schematic representations of another embodiment of the invention in an expanded position.

Referring to FIGS. 3A-3B, in another embodiment, ureteral stent 300 has an elongated member 310 including a spring 315. Distal retention structure 125 is connected to a distal end 312 of elongated member 310, and proximal retention structure 135 is connected to a proximal end 314 of elongated member 310.

Spring 315 has a plurality of coils 320 having, in some embodiments, a spring force less than one pound. Spring 315 includes a wire 325 formed from a superelastic material. Materials with superelastic properties make it possible to conFIG. a component into a particular shape, such as a coil or a sleeve, and then modify reversibly the geometry of the component, such as by straightening it out. Once the device is straightened, after removal of the straightening force, the component reverts spontaneously to its predetermined configuration, thereby regaining its former geometry. In so doing, the component provides a biasing force back to its original configuration.

Superelastic materials can include alloys of In—Ti, Fe—Mn, Ni—Ti, Ag—Cd, Au—Cd, Au—Cu, Cu—Al—Ni, Cu—Au—Zn, Cu—Zn—Al, Cu—Zn—Sn, Cu—Zn—Xe, $Fe_3Be$, $Fe_3Pt$, Ni—Ti—V, Fe—Ni—Ti—Co, and Cu—Sn. Preferably, wire 325 includes a superelastic material comprising a nickel and titanium alloy, known commonly as nitinol, available from Memory Corp. of Brookfield, Conn. or SMA Inc. of San Jose, Calif. The ratio of nickel and titanium in nitinol can be varied. Examples include a ratio of about 50% to about 52% nickel by weight, or a ratio of about 48% to about 50% titanium by weight. Nitinol has shape retention properties in its superelastic phase.

Wire 325 can have a coating 330 including a biocompatible material, such as a polymer like urethane, nylon, TPU, thermoplastic polyester elastomer, polyethyl, or silicone. Coating 330 can be applied to wire 325 by various methods, such as spray coating or painting.

Figure 4A:
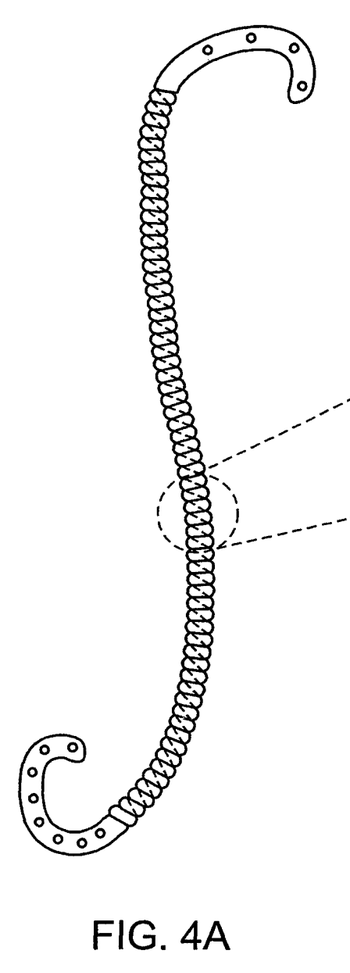
FIGS. 4A-4C are schematic representations of the embodiment of the invention illustrated in FIGS. 3A-3B in a retracted position.
Figure 4B:
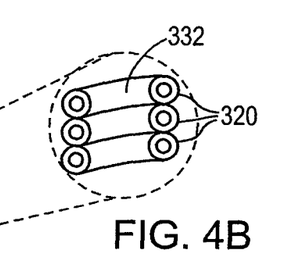
Figure 4C:
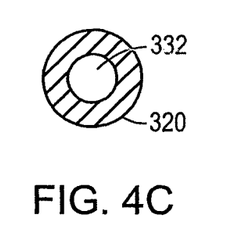

Ureteral stent 300 has an expanded position (see, e.g., FIG. 3A-3B) and a retracted position (see, e.g., FIGS. 4A-4C). In the retracted position, coils 320 abut each other, defining a lumen 332 that is substantially enclosed. In the expanded position, coils 320 define a spiral-shaped opening 335, formed by a plurality of gaps 340 between coils 320. Elongated member 310 is linearly expandable along a longitudinal axis 345 of lumen 332.

Figure 5A:
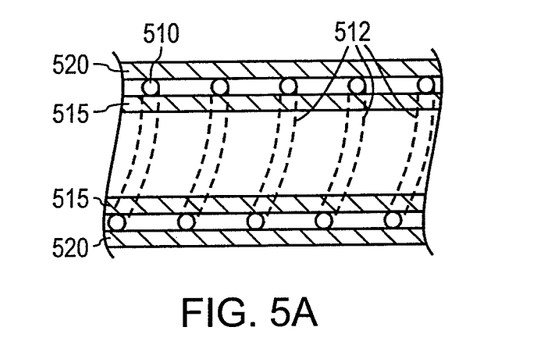
FIGS. 5A-5C are schematic representations of yet another embodiment of the invention at various stages of fabrication.
Figure 5B:
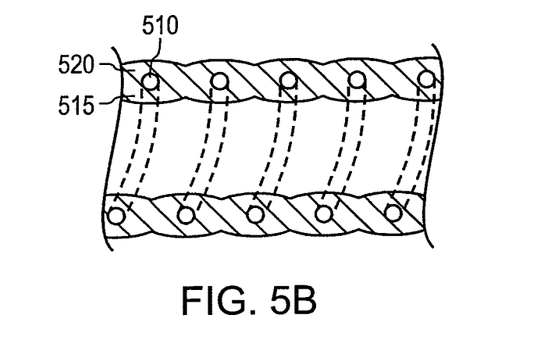
Figure 5C:
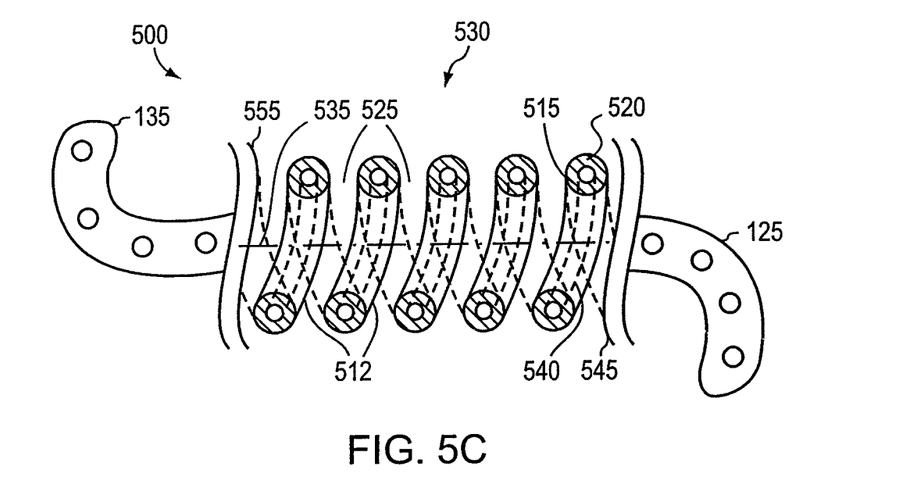

Referring to FIGS. 5A-5C, in another embodiment, a stent 500 is formed by placing a wire spring 510, having a plurality of coils 512, between an inner lining 515 and an outer cover 520. Wire spring 510 can be made from a metal alloy including, for example, titanium, nickel, copper, cobalt, vanadium, or iron. The metal alloy can include nitinol, a material including nickel and titanium. Inner lining 515 and outer cover 520 can each be formed from an extruded sheet. Inner lining 515 and outer cover 520 can each be made from a polymer, such as urethane, nylon, TPU, thermoplastic polyester elastomer, polyethyl, and silicone.

Inner lining 515 and outer cover 520 are deformed at elevated temperatures to fully surround wire spring 510. For example, inner lining 515 and outer cover 520 can be shrunk by, e.g., exposure to a heat lamp. Alternatively, inner lining 515 and outer cover 520 can be melted by, e.g., heating in an oven. After deformation, a plurality of slits 525 are formed through inner lining 515 and outer cover 520 between coils 512 to form an elongated member 530. Elongated member 530 is linearly expandable along a longitudinal axis 535 of a lumen 540 extending through elongated member 530. Elongated member 530 is connected at a distal end 545 to a distal retention structure 125, and at a proximal end 555 to a proximal retention structure 135.

Figures 6A, 6B, 6C:
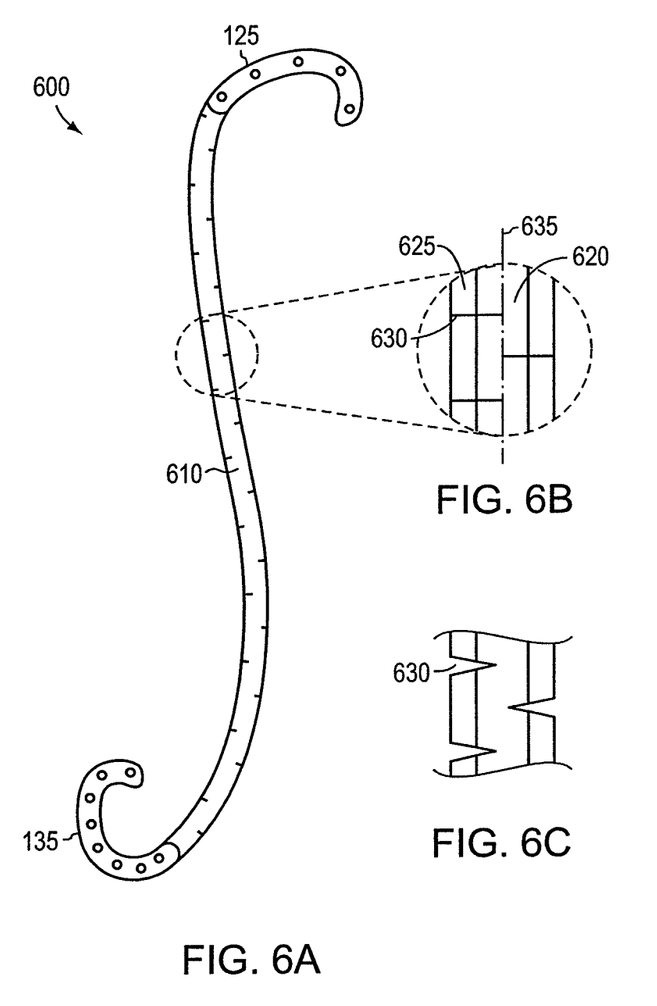
FIGS. 6A-6C are schematic representations of yet another embodiment of the invention in retracted and expanded positions.

Referring to FIGS. 6A-6C, in yet another embodiment, a stent 600 has an elongated member 610 connected to distal retention structure 125 for retention in a kidney and proximal retention structure 135 for retention in a bladder. Elongated member 610 defines a lumen 620, and has a solid sidewall 625. Solid sidewall 625 can be made of a biocompatible material, such as a polymer, e.g., urethane, nylon, TPU, thermoplastic polyester elastomer, polyethyl, or silicone. Solid sidewall 625 has at least one slit 630 formed in it, so that elongated member 610 is linearly expandable along a longitudinal axis 635 of lumen 620.

Figure 7:
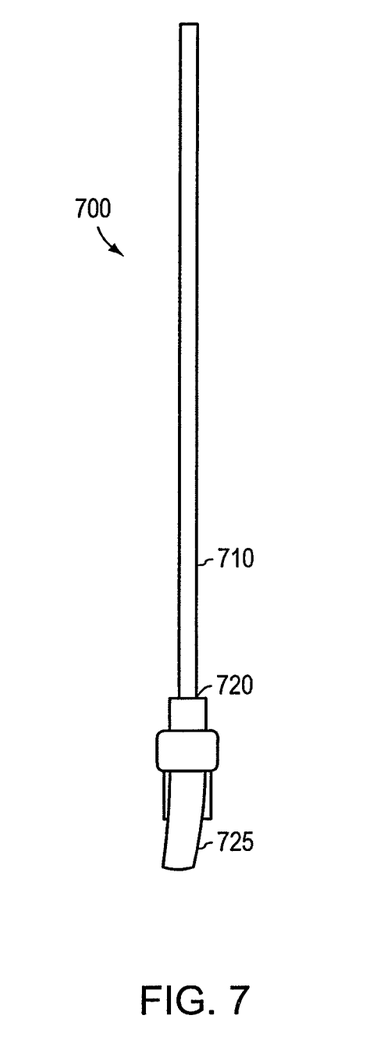
FIG. 7 is a schematic representation of an introducer.

Referring to FIG. 7, in another aspect, the invention provides an apparatus for delivering a stent into a patient. An introducer 700 includes a guide wire 710. A proximal end 720 of guide wire 710 includes a grip 725 to assist in using the device.

Referring to FIG. 7 and also to FIG. 1A, in use, a stent, (e.g., stent 120) is mounted on introducer 700. Distal retention structure 125 is threaded over guide wire 710, and most of its inherent curvature is removed. Next, the guide wire 710 is inserted into bladder 115 through ureteral orifice 136 up ureter 105, and into kidney 110. A pusher (not shown) is then moved along guide wire 710, pushing stent 120 along guide wire 710 towards kidney 110. Proximal end 144 of elongated member 140 can be positioned either at or distal to ureteral orifice 136. Stent 120 can also be positioned such that proximal retention structure 135 is at or distal to ureteral orifice 136.

Once the surgeon has achieved the desired positioning of stent 120, guide wire 710 is removed, while holding the pusher stationary to maintain stent 120 in position. Finally, the pusher is removed from within the patient, leaving stent 120 in place. Using this method, the stent of the invention can be precisely positioned within ureter 105 of the patient. The method can also be used to accurately position proximal retention structure 135 in bladder 115, and distal retention structure 125 within kidney 110.

In one embodiment of the invention, the guide wire, pusher, and stent are inserted into ureter 105 percutaneously through a surgical opening. In another embodiment, they are inserted into the ureter via the urinary tract of the patient.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A ureteral stent comprising:
    a tube including a distal end and a proximal end, the tube having an inner diameter and an outer diameter, the inner diameter of the tube defining an internal lumen extending along a length of the tube, the tube being solid from the inner diameter to the other diameter, the tube having a slit such that the slit defines a spiral-shaped opening with a plurality of rotations, the slit extending through the tube to the internal lumen, the tube configured to move between a retracted configuration and an expanded configuration along a longitudinal axis of the internal lumen; and
    a distal retention structure disposed at the distal end of the tube for retention in a kidney, the distal retention structure defining an internal lumen through a body of the distal retention structure, the internal lumen of the distal retention structure being in fluid communication with the internal lumen of the tube, the internal lumen defined by the distal retention structure having a portion that extends away from the longitudinal axis of the internal lumen of the tube, the distal retention structure having a curved shape when in a first configuration,
    wherein the distal retention structure is configured to receive a guide wire such that the guide wire extends through the internal lumen of the distal retention structure when in a second configuration different than the first configuration,
    wherein the distal retention structure has most of its curvature removed when in the second configuration.

2. The ureteral stent of claim 1, wherein the distal retention structure defines an opening to the internal lumen of the distal retention structure on an end portion of the distal retention structure, the tube defining an opening to the internal lumen of the tube on an end portion of the tube wherein the opening to the internal lumen of the distal retention structure is exposed to the opening to the internal lumen of the tube such that the internal lumen of the distal retention structure is in fluid communication with the internal lumen of the tube.

3. The ureteral stent of claim 1, wherein the tube includes a single monolithic tube, and the internal lumen of the tube is defined by a cavity extending into the single monolithic tube.

4. The ureteral stent of claim 1, wherein the tube includes a polymer material, and the distal retention structure is a nylon or polyurethane.

5. The ureteral stent of claim 1, wherein a portion of the distal retention structure has a shape selected from a group consisting of a "J" shape, a coil shape, a pig-tail coil shape and a helical coil shape.

6. The ureteral stent of claim 1, further comprising a proximal retention structure disposed at a proximal end of the tube for retention in a bladder.

7. The ureteral stent of claim 6, wherein a portion of the proximal retention structure has a shape selected from a group consisting of a "J" shape, a coil shape, a pig-tail coil shape and a helical coil shape.

8. The ureteral stent of claim 1, wherein the tube is configured to move between the retracted configuration and the expanded configuration along the longitudinal axis in response to relative movement between the kidney and the bladder.

9. The ureteral stent of claim 1, wherein the tube includes a first material, and the distal retention structure includes a second material, a portion of the first material being coupled to a portion of the second material.

10. A ureteral stent comprising:
    a tube having a proximal end and a distal end, the tube having an inner diameter and an outer diameter, the inner diameter of the tube defining an internal lumen extending along a length of the tube when the tube is in a refracted configuration, the tube being solid from the inner diameter to the outer diameter, the tube having a slit such that the slit defines a spiral-shaped opening with a plurality of rotations, the slit extending through the tube to the internal lumen, the tube being configured to move between the retracted configuration and an expanded configuration along a longitudinal axis of the tube; and
    a distal retention structure disposed at the distal end of the tube for retention in a kidney, the distal retention structure defining an internal lumen through a body of the distal retention structure, the internal lumen of the distal retention structure being in fluid communication with the internal lumen defined by the inner diameter of the tube when the tube is in the retracted configuration, the distal retention structure having a first portion that extends away from the longitudinal axis of the tube and a second portion extending from the first portion and extending toward the proximal end of the tube, the distal retention structure having a curved shape when in a first configuration,
    wherein the distal retention structure is configured to receive a guide wire such that the guide wire extends through the internal lumen of the distal retention structure when in a second configuration different than the first configuration,
    wherein the distal retention structure has most of its curvature removed when in the second configuration.

11. The ureteral stent of claim 10, wherein the tube has a cross-section when the tube is in the expanded configuration, the cross-section being substantially quadrilateral in shape.

12. The ureteral stent of claim 10, wherein a portion of the distal retention structure has a shape selected from a group consisting of a "J" shape, a coil shape, a pig-tail coil shape and a helical coil shape.

13. The ureteral stent of claim 10, further comprising a proximal retention structure disposed at a proximal end of the tube for retention in a bladder.

14. The ureteral stent of claim 10, wherein the inner diameter of the tube that defines the internal lumen of the tube has a first value when the tube is in the expanded configuration, and the inner diameter of the tube that defines the internal lumen of the tube has a second value when the tube is in the retracted configuration, the second value being greater than the first value.

* * * * *